(12) United States Patent
Farwell

(10) Patent No.: US 7,689,272 B2
(45) Date of Patent: Mar. 30, 2010

(54) METHOD FOR BRAIN FINGERPRINTING, MEASUREMENT, ASSESSMENT AND ANALYSIS OF BRAIN FUNCTION

(76) Inventor: Lawrence Farwell, P.O. Box 176, Fairfield, IA (US) 52556

( * ) Notice: Subject to any disclaimer, the term of this patent is extended or adjusted under 35 U.S.C. 154(b) by 1523 days.

(21) Appl. No.: 10/163,525

(22) Filed: Jun. 7, 2002

(65) Prior Publication Data

US 2002/0188217 A1 Dec. 12, 2002

Related U.S. Application Data

(60) Provisional application No. 60/296,222, filed on Jun. 7, 2001.

(51) Int. Cl.
*A61B 5/04* (2006.01)

(52) U.S. Cl. .................................................. 600/544

(58) Field of Classification Search ................ 600/300, 600/301, 544, 545, 558
See application file for complete search history.

(56) References Cited

U.S. PATENT DOCUMENTS

| | | | | |
|---|---|---|---|---|
| 4,987,903 A | * | 1/1991 | Keppel et al. ............... 600/545 |
| 5,137,027 A | * | 8/1992 | Rosenfeld .................... 600/544 |
| 5,467,777 A | * | 11/1995 | Farwell ....................... 600/544 |
| 5,622,181 A | * | 4/1997 | Rosenfeld .................... 600/544 |
| 5,846,189 A | * | 12/1998 | Pincus ......................... 600/301 |
| 6,434,419 B1 | * | 8/2002 | Gevins et al. ................ 600/544 |
| 6,463,321 B2 | * | 10/2002 | Granger ....................... 600/544 |

* cited by examiner

*Primary Examiner*—Max Hindenburg
*Assistant Examiner*—Jonathan M Foreman

(57) ABSTRACT

Electrical signals originating in the brain are measured and analyzed. In one embodiment, this technology serves to assess brain functioning as a means to evaluate cognitive functioning, to detect cognitive deficits such as those brought about by Alzheimer's, and to assess the efficacy of treatments for cognitive disorders. In another embodiment, which is an improvement on technology previously patented by the inventor, this technology serves to detect information in the brain as a means of detecting participation in specific organizations, acts, or criminal activity. In a third embodiment, this technology serves to evaluate the effectiveness of advertising, educational and training presentations by detecting the attention, information processing, and memory-related responses to these presentations as revealed by brain waves.

28 Claims, 2 Drawing Sheets

METHOD FOR BRAIN FINGERPRINTING, MEASUREMENT, ASSESSMENT AND ANALYSIS OF BRAIN FUNCTION

RELATED PROVISIONAL APPLICATION AND PATENTS

This application claims the benefit of U.S. Provisional Appln. No. 60/296,222, filed Jun. 7, 2001 and relates to prior U.S. Pat. No. 5,363,858 entitled "Method and Apparatus for Multifaceted Electroencephalographic Response Analysis (MERA);" U.S. Pat. No. 5,406,956 entitled "Method and Apparatus for Truth Detection;" and U.S. Pat. No. 5,467,777 entitled "Method for Electroencephalographic Information Detection;" all of common inventorship with the subject application. The disclosures of these prior patents are hereby incorporated by reference.

BACKGROUND OF THE INVENTION

Field of the Invention

The present invention relates to a method and apparatus for Brain Fingerprinting, measurement, assessment and analysis of brain function.

Detection of Concealed Information through Electrical Brain Responses

The invention relates to applicant's prior patented technology which is no commonly known as Brain Fingerprinting. Brain Fingerprinting has been extensively tested and proven, and clear scientific protocols and techniques have been established for its implementation. The science involved in Brain Fingerprinting has been thoroughly tested, proven highly accurate, and extensively peer reviewed and published. This science is widely accepted in the relevant scientific community. Brain Fingerprinting has been admitted as evidence in court. Refinements in the technology, however, are still both possible and valuable.

The basic bootstrapping data analysis algorithm now incorporated in Brain Fingerprinting has proved to be highly effective in detecting concealed information stored in the brain, including not only laboratory research but also cases of detecting information regarding real-life events. Nevertheless, additional, more sophisticated data analysis techniques can add to the efficacy of the technology, particularly in demanding field situations. The advanced data analysis techniques that show promise for improving the efficacy of Brain Fingerprinting include bootstrapping on unweighted double-centered correlations, bootstrapping on single centered correlations, bootstrapping on positive and negative areas and peaks, covariance with a template, stepwise linear discriminant analysis, dynamical systems (chaos) analysis, frequency domain analysis, bootstrapping on the frequency spectra, time-frequency analysis, and multiple-electrode correlations.

Moreover, refinements of the Brain Fingerprinting technology, as described below, can be applied to address criminal activity. A central problem in investigating criminal activity is twofold: 1) to identify the perpetrators of criminal acts that have already occurred, and 2) to identify criminals who are trained to accomplish specific crimes before they strike. Brain Fingerprinting addresses both of these needs.

Brain Fingerprinting detects information stored in the human brain with extremely high accuracy by measuring electrical brain responses to information presented on a computer screen. The brain response to known information—that is, information that matches the information stored in the brain—is clearly distinguishable from the brain response to unknown information.

Brain Fingerprinting has proven to be extremely effective in detecting information stored in the brain regarding actual crimes and many other situations. In the same way, this scientific technology can be used to identify those who have perpetrated specific criminal acts or have helped in the planning of these acts. Brain Fingerprinting thus can provide a key capability in the investigation of criminal activity.

Moreover, Brain Fingerprinting can detect individuals trained in methods for perpetrating crimes before they strike. If Brain Fingerprinting can detect an FBI agent by measuring brain responses to information known only to FBI agents, we can use the same technology to detect an individual who has had specific crime-related training or indoctrination not known to the general public, or who is a member of a specific criminal group, by measuring brain responses to information uniquely known to such individuals. Innocent people who may have fallen under suspicion for any reason can be cleared of suspicion and allowed to go on with their lives.

The difficulties, limitations and desires suggested in the preceding are not intended to be exhaustive, but rather are among many which demonstrate that prior art methods and systems for Brain Fingerprinting will admit to worthwhile improvement.

Overview of Brain Fingerprinting

Electrical Brain Responses as a Diagnostic Tool

An effective diagnostic tool must be based on a specific and sophisticated understanding of that which is to be diagnosed. Progress in the development of a diagnostic tool involves developing an increasingly specific and sophisticated definition of the phenomenon to be diagnosed, and developing objective measures that bring under experimental control critical aspects of the phenomenon to be measured.

Considerable progress along these lines has taken place towards the goals of developing brain-wave-based measures of the normal aging process and diagnostic tools for Alzheimer's and other aging-related disease processes. Two reviews of the literature on event-related brain potentials and aging that have been published by the inventor and his colleagues outline some of the major milestones in this progress. One was published in *Progress in Brain Research, Volume 70: Aging of the Brain and Alzheimer's Disease*, the other in *Annual Review of Gerontology and Geriatrics, Volume 7*.

Initial attempts to study the aging brain through the use of brain-wave measurements used frequency analysis of brain waves in situations where no specific tasks were assigned. It was discovered that there was a generalized reduction in the frequency of brain waves in aging. Such measurements were inevitably imprecise, however, due to two major factors. First of all, frequency analysis (dividing the electroencephalographic output into alpha waves, beta waves, etc.) provides only a very coarse and non-specific picture of electroencephalographic activity. Second, and more importantly, measuring brain waves in a situation where the subject is given no instructions other than to sit and have his brain waves measured fails to bring under experimental control the relevant phenomena. In the absence of any assigned task, there is an extremely wide variety of things that a subject may be doing with his brain during the process of sitting and having his brain waves measured. Thus, there will be wide variability in the results of any measurement, and the more accurate the metric is in reflecting what is going on in the brain, the greater the variability of results.

The fact is that the brain is not a simple generator of neuronal impulses that can be measured at the scalp electroencephalographically. It is an extremely complex system with widely varying functions that can be implemented in response to widely varying tasks. The results of measurements of its activity depend on what it is doing at the time. Some of the algorithms it can implement are relevant to aging and/or Alzheimer's, and some are not. Thus, the utility, specificity, and diagnostic value of simple measurements of brain waves in the absence of specific tasks will inevitably be severely limited, particularly in cases such as Alzheimer's where the relevant deficits are in higher-order brain processes.

The next phase of progress in the measurement of brain functioning in aging and disease processes came with the introduction of specific stimuli while brain waves were being measured. It was found, for example, that peripheral nerve degeneration (in the sensory systems) could be measured by the automatic response to changing visual patterns presented to the subject on a computer screen. This process of measuring responses to sensory stimuli resulted in a useful diagnostic tool for measuring the progress of MS, which affects the speed of nerve conduction in the peripheral sensory nervous system.

The measurement of brain-wave responses to sensory stimuli, however, also has inevitable limitations. Such metrics are useful when what is being measured is a peripheral process that is entirely driven by the stimulus presented. In aging, Alzheimer's, and many other disease processes, the brain functions affected are not peripheral sensory processing, but rather highly complex central nervous system information-processing functions.

The brain is much more than a simple stimulus-response box. It is a highly complex system, capable of highly complex information-processing activities that vary depending not only on the sensory stimulus, but also on the state, perceived tasks, tactics, strategies, and information-processing algorithms implemented by the subject. Any system that will stand a chance of being an effective diagnostic tool for deficits in memory, cognitive tasks, and other higher-order processes that are affected by aging and by Alzieimer's must necessarily accomplish two goals. It must differentially elicit the relevant processes (e.g., memory access), and it must differentially measure the functioning of the brain when these processes are implemented. Only by achieving a high level of specificity in task demands and metrics to assess the brain's activities while accomplishing these tasks is ft possible to achieve an adequate diagnostic metric. As is discussed in some detail in the two attached review articles by Dr. Farwell and his colleagues, previous unsuccessful attempts to utilize brainwaves diagnostically have generally failed to take this requirement into account, and have relied on an unrealistically simplistic view of the brain and the information processing it carries out.

A rather extensive body of research exists, however, where scientists have taken into account the richness and complexity of the information-processing activities undertaken by the brain, and the need to bring these different activities under experimental control and to differentially measure their electroencephalographic manifestations. This field has progressed to the point where it shows great promise for developing electroencephalographic diagnostic tools and metrics for aging, Alzheimer's, and other aging-related disease processes.

It has long been known that elderly people accomplish tasks more slowly than younger people, and that people with Alzheimer's accomplish some of these tasks even more slowly. Take, for example a task where a subject must read a phrase flashed on a computer screen, determine whether or not it is in an assigned memory set, and push one of two buttons indicating his response. It comes as no surprise that older people perform this task more slowly than younger people.

Early theories of aging held that this kind of effect was due to a generalized, non-specific slowing of neuronal functioning in aging. Event-related potential research, however, has disproved this hypothesis, by enabling scientists to parse the different phases of the information-processing, sensory, and motor activity that comprise the task.

Note that the overall task under consideration involves some information-processing activities, such as a memory search, that are relevant to the deficits produced by Alzheimer's, and other activities, such as physically moving the thumb down on a button, that are not. In developing diagnostic tools and metrics relevant to important central-nervous-system decline in functioning due to aging, and in particular deficits due to Alzheimer's, we are concerned with higher-order information-processing, and not with purely motor or sensory deficits. That portion of the age-related slowing that takes place as a result of the fact that old peoples' thumbs move more slowly than those of the young is not of interest in this context. The aspect of the task that involves a memory search, however, is of considerable interest and relevance.

By parsing the task into its specific information-processing components—which are observable through electroencephalographic measures but are not observable through overt behavior—research in event-related brain potentials has shed considerable light on the locus of slowing in aging. Contrary to early theories, this slowing is not uniform across all neuronal activities and processes. Specifically, event-related potential research showed that in the memory task described above, there was little or no slowing in the actual component of the process that involved memory search. In normal subjects, the age-related slowing took place in several phases: 1) evaluation of the stimulus; 2) response selection; 3) the adoption of a more conservative strategy emphasizing accuracy rather than speed in the elderly (which is not a deficit); and 4) motor activity.

These results were found in the case of normal aging in the absence of disease processes. With Alzheimer's and the well-established concomitant memory and cognitive deficits, we would expect a different picture. In Alzheimer's patients, we would expect a slowing not only in those aspects of the task that slow with normal aging, but also a slowing in the memory search process itself. This is a process that is amenable to precise measurement through event-related potential measurements using the P300 component, one of the major components used by Dr. Farwell in the forensic applications of Brain Fingerprinting.

There has been some preliminary progress already in using event-related potentials, in particular the P300, in the differential diagnosis of dementia. Research has shown substantial increase in the latency of P300 in demented subjects that was not found in subjects showing very similar outward symptoms due to depression rather than dementia, nor was it found in normal elderly subjects.

Such results show that event-related brain potentials and other related electroencephalographic technologies hold significant promise for developing a viable technology for diagnosis of Alzheimer's, tracking of the progress of the disease, and quick and objective evaluation of the effectiveness of treatment.

Electrical Brain Responses as a Forensic Tool

Brain Fingerprinting detects the record of a crime or other act stored in the brain of a perpetrator. It can detect trained criminals or members of criminal groups before they strike. It is also capable of exonerating innocent suspects quickly and non-stressfully.

A. A Technique of Proven Accuracy in US Government Tests

Brain Fingerprinting is a new computer-based technology to detect the record of a crime stored in the brain of a perpetrator accurately and scientifically by measuring brain-wave responses to crime-relevant words or pictures presented on a computer screen. Brain Fingerprinting has proven accurate to date in tests, including tests on FBI agents, tests for the CIA and for the US Navy, and tests on real-life situations including actual crimes.

B. Scientific Detection of the Record of the Crime in the Perpetrator's Brain

Brain Fingerprinting is based on the principle that the brain is central to all human acts. In a criminal act, there may or may not be many kinds of peripheral evidence, but the brain is always there, planning, executing, and recording the crime. The fundamental difference between a perpetrator and a falsely accused, innocent person is that the perpetrator, having committed the crime, has the details of the crime stored in his brain, and the innocent suspect does not. This is what Brain Fingerprinting detects scientifically.

C. Matching Evidence from a Crime Scene with Evidence on the Perpetrator

Brain Fingerprinting matches evidence from a crime scene with evidence stored in the brain of the perpetrator, similarly to the way conventional fingerprinting matches fingerprints at the crime scene with the fingers of the perpetrator, and DNA fingerprinting matches biological samples from the crime scene with the DNA in the body of the perpetrator.

D. Applicability of Brain Fingerprinting

DNA and conventional fingerprinting are extremely accurate techniques. DNA and fingerprints, however, are found in only a small percent of crimes. Even with a low percent of applicability, however, these techniques are highly valuable. Brain Fingerprinting has a much wider applicability than DNA and conventional fingerprinting. The brain is always there, planning, executing, and recording the crime. All that is necessary for Brain Fingerprinting to be applicable in a particular case is that the investigators properly collect and preserve the necessary evidence of the specific details of what happened, so that suspects can be tested for knowledge of these details. Even with no improvement in present methods (where investigators do not typically collect and preserve evidence in an optimal way to apply the technique), Brain Fingerprinting can be applied in approximately 10% of criminal investigations.

E. Brain Fingerprinting Found Admissible in Court in Murder Case

On Apr. 25, 2000, Dr. Farwell used Brain Fingerprinting to test a man who has spent 23 years in prison for murder. In March, 2001 an Iowa judge ruled Brain Fingerprinting admissible in the Terry Harrington case. The judge did not, however, grant him a new trial. Harrington is appealing the decision denying him a new trial to the Iowa Supreme Court, seeking a new trial based on Brain Fingerprinting and other evidence.

Harrington was convicted in 1978 of the murder of a retired policeman who was working as a security guard, based primarily on the testimony of an alleged witness who was himself involved in the crime.

Brain Fingerprinting proved that Harrington's brain did not contain details of the crime that the perpetrator would have encountered in committing the crime. Brain Fingerprinting proved that the record stored in Harrington's brain did not match the crime scene, and did match Harrington's alibi.

After the Brain Fingerprinting test, the only alleged witness to the crime—whose testimony was the primary basis for Harrington's conviction—recanted his testimony and admitted under oath that he did not witness Harrington committing the crime. Legal efforts to win Harrington's freedom based on Brain Fingerprinting and other newly discovered exculpatory evidence are ongoing.

F. How the Technology Works

Brain Fingerprinting works as follows. Words, phrases, or pictures relevant to a crime are flashed on a computer screen, along with other, irrelevant words or pictures. Electrical brain responses are measured non-invasively through a headband equipped with sensors. It has been well established scientifically that a specific brain-wave response is elicited when the brain processes noteworthy information it recognizes. A thoroughly researched response that is elicited by this recognition process is known as a P300. Dr. Farwell has discovered that the P300 is a part of a more comprehensive response known as a MERMER (memory and encoding related multifaceted electroencephalographic response). Thus, when details of the crime that only the perpetrator would know are presented, a P300 and a MERMER are emitted by the brain of a perpetrator, but not by the brain of an innocent suspect. In Brain Fingerprinting, a computer analyzes the brain response to detect the P300/MERMER, and thus determines scientifically whether or not the specific crime-relevant information is stored in the brain of the suspect.

G. Scientific Experiments, Field Tests, and Criminal Cases

Five scientific studies, along with field tests and actual criminal cases, involving over 170 individuals, are described in various scientific publications and technical reports by Dr. Lawrence A. Farwell and his colleagues. These scientific tests have verified the extremely high level of accuracy, effectiveness, and utility of Brain Fingerprinting. Since the discovery of the MERMER, Brain Fingerprinting has had highly accurate scientific results in studies, field tests, and actual cases conducted to date. Brain Fingerprinting has been thoroughly tested and proven both in the laboratory and in the field. Of the 170 tests conducted, over 80 were real-life tests involving detecting information regarding actual, real-life events, and the rest were laboratory studies.

1. Federal Bureau of Investigation (FBI) Studies

Brain Fingerprinting had 100% accurate scientific results in distinguishing 17 FBI agents and 4 non-FBI agents from a group of 21 subjects. The detection of FBI agents indicates that the system could detect members of a criminal organization as well as perpetrators of a specific crime. In Experiment 1, the information detected was specific knowledge that would identify an individual as an FBI agent. The purpose of this experiment was to determine whether this method could be useful in detecting members of a group or organization or people with a particular knowledge. Stimuli were words, phrases, and acronyms flashed on a computer screen. Experiment 2 at the FBI correctly detected whether or not individuals had participated in specific, real-life events.

2. Brain Fingerprinting Catches a Serial Killer

On Aug. 5, 1999 Dr. Farwell used Brain Fingerprinting to test the brain of suspected serial killer James B. Grinder for the details of the rape and murder of Julie Helton that had occurred 15 years earlier. The Brain Fingerprinting test showed that Grinder's brain clearly contained a comprehensive record of the crime. Faced with an almost certain conviction and probable death sentence, Grinder pleaded guilty one week later in exchange for a sentence of life in prison without parole. He is currently serving that sentence, and has confessed to the murders of several other young women.

3. Brain Fingerprinting Found Admissible in Court in Murder Case

On Apr. 25, 2000, Dr. Farwell used Brain Fingerprinting to test Terry Harrington, a man who has spent 23 years in prison for murder. Brain Fingerprinting showed that the record stored in his brain did not match the crime scene and did match his alibi. In January, 2001 an Iowa judge ruled Brain Fingerprinting admissible in the Harrington case. He found that Brain Fingerprinting was scientifically tested and proven, peer reviewed and published, accurate, and well accepted in the scientific community, thus meeting the standard for admissibility in court. Harrington is currently appealing for a new trial based on this and other evidence.

H. Results of Research, Field Tests, and Investigations

All of the subjects in the above experiments were correctly classified as possessing or not possessing the critical information. There were no false positives, no false negatives, and no indeterminates. In the two murder cases described above, the results of the Brain Fingerprinting tests were corroborated by substantial independent evidence. In one criminal case, Brain Fingerprinting vindicated a police officer falsely accused of a felony. In another actual criminal case, brain responses of two subjects showed that one subject was present at an armed robbery, and the other knew nothing of the crime. Brain Fingerprinting correctly classified both subjects. In all of these studies and cases, words, phrases, or pictures flashed on a computer screen containing information relevant to the crimes or other situations elicited a P300 and a MERMER only in the subjects who possessed the critical information.

New Refinements of Brain Fingerprinting

In the past, Brain Fingerprinting has proven effective in information detection and forensic applications. Refinements in the technology, described below, improve the effectiveness of Brain Fingerprinting, and make Brain Fingerprinting a more effective tool in fighting crime.

Applications of Brain Waves in Advertising, Training, and Education

As described above, brain waves can provide information regarding what information is stored in a brain, and how effectively an individual is processing information. In the evaluation of advertising and training programs, what is important is how effective a particular advertisement or training protocol is in imparting information and stimulating attention, understanding, and retention of material. The window into the brain provided by brain waves can address this need as well. Differences in brain responses can reveal how different advertising and training programs affect the information processing accomplished in the brains of the individuals viewing or participating in these programs. This is described in more detail below.

It is, therefore, a general object of the invention to provide a method and apparatus for Brain Fingerprinting, measurement, assessment and analysis of brain function in aging and Alzheimer's disease, which utilizes software and hardware to promote, record, amplify and analyze brainwave activity in a subject.

It is another general object of the invention to provide a method and apparatus for discovering what information is stored in a subject's brain.

It is another general object of the invention to provide a method and apparatus for analyzing how effectively a brain is functioning.

It is another general object of the invention to provide a method and apparatus for analyzing how brain functioning is affected by outside influences.

It is a specific object of the invention to provide a method and apparatus for diagnosing cognitive disorders and making assessments of treatment effectiveness for such disorders, utilizing data recorded from brainwave activity when a subject is provided with stimuli.

It is another specific object of the invention to provide a method and apparatus for developing evidence for use in forensic science, utilizing data analysis of brainwave activity to distinguish whether a subject recognizes relevant information.

It is another general object of the invention to provide a method and apparatus for evaluating the effectiveness of advertising, education, and training programs; utilizing data analysis of brainwave activity to determine how effective the programs are in imparting information, stimulating attention, understanding and retention of material.

It is another general object of the invention to provide a method of improving the performance of Brain Fingerprinting methods, such as those listed above, by employing data analysis and signal processing techniques such as bootstrapping on unweighted double-centered waveforms as well as other techniques.

SUMMARY OF THE INVENTION

To achieve at least some of the foregoing objects, the subject invention provides a method and apparatus for Brain Fingerprinting, measurement, assessment and analysis of brain function. Brain waves provide a window into the brain. This invention comprises a technology for using brain waves to discover what information is stored in a brain, how effectively that brain is functioning, and how the functioning of that brain is affected by various outside influences.

This technology has several related embodiments, each with a different set of applications, as follows.

Medical: Diagnosis of cognitive disorders and assessments of treatment effectiveness. By detecting how the brain processes information, we can shed light on how effectively the brain is functioning and objectively measure the speed of certain information-processing brain activities that are not directly observable through overt behavior. This allows for an objective assessment of cognitive functioning and cognitive deficits. This technology can provide an objective test for cognitive deficits resulting from diseases such as Alzheimer's, potentially yielding a means of early diagnosis and an objective way to measure the progress of the disease and the effectiveness of treatments. This is accomplished by presenting the subject with tasks which have a significant cognitive component and measuring the electrical brain activity undertaken in response to these tasks. By varying the difficulty of the tasks and measuring the brain's response to changes in task difficulty, additional information can be obtained on how well the brain is functioning cognitively.

Forensic Science: Improvements in Brain Fingerprinting. By determining what information is stored in a brain, it is possible to develop evidence regarding what events a person has participated in. This allows authorities to distinguish, for example, between a person intimately involved in a crime and an innocent individual, or between a person who was involved in planning specific crimes and an innocent person. This is accomplished by presenting on a computer screen words or pictures depicting details of the situation under investigation, mixed in with other, irrelevant items. A characteristic brain response, which can be detected through signal-analysis techniques, reveals whether or not the subject recognizes the relevant information as significant. This invention constitutes further refinements and improvements of the basic technology embodied in three previous patents Issued to the inventor.

Advertising, Education, and Training: Evaluating the effectiveness of advertising, educational, and training presentations. By detecting how the brain processes information, this technology can shed light on what methods of reaching and teaching an individual are most effective. In the advertising field, brain-wave measurements can reveal the effectiveness of advertising presentations in eliciting a high level of attention from subjects, in making critical items noticeable and salient, and in imparting a message that is later remembered. This is accomplished by measuring brain responses indicating recognition or attention during the presentation of advertising presentations, and also by measuring brain responses during later presentation of items that have been previously viewed by a subject in an advertisement. Similarly, brain waves can shed light on the effectiveness of training and educational presentations in eliciting attention, in stimulating the subject to notice and process critical information, and in presenting information in such a way that it is retained.

The subject technology is directed to a method of assessing one or more of the following conditions: cognitive functioning; cognitive deficits; efficacy of treatments for cognitive deficits; mental deterioration due to disease processes; mental deterioration due to trauma; mental deterioration due to aging; mental deterioration due to Alzheimer's disease; and efficacy of treatments for said mental deterioration. The method includes assigning a task that has cognitive and non-cognitive aspects, measuring behavioral output of said task and a timing of said output, measuring and analyzing brain responses that provide an index of specific cognitive processes; and evaluating cognitive functioning and deficits based on said brain responses. In a further embodiment, the timing of said brain responses is measured, and the evaluation is accomplished using metrics that include differences in the time course of the responses. In a further aspect, the cognitive task involves classifying and differentially responding to items according to a classification rule, and the difficulty of the cognitive task is manipulated by at least one of varying the classification rule, varying the items to be classified, varying the number of items to be classified, and varying the type of items to be classified. In a further aspect, the difficulty of cognitive tasks is systematically manipulated, and the brain responses and timing thereof in performing tasks of varying levels of difficulty may be compared.

DRAWINGS

Other objects and advantages of the present invention will become apparent from the following detailed description of preferred embodiments thereof taken in conjunction with the accompanying drawings, wherein.

DETAILED DESCRIPTION

Description of Preferred Embodiments

A. Detection of Concealed Information

1. Refinements in Experimental Design

A full understanding of the optimum application of Brain Fingerprinting includes advancements in the understanding of the memory-related phenomena that contribute to the brain information processing that yields the information detection. The effectiveness of Brain Fingerprinting can be optimized by manipulating various factors that may affect memorability of events. Factors to be systematically manipulated include time elapsed since the event, level of participation, repetitions, salience, complexity of information, relationship of relevant information with other well-recalled information, episodic versus semantic memory, affect at the time of encoding, self-referral nature of the information, action orientation of the information, and degree to which the information is consequential.

2. Equipment and Technology—Real-Time Remote Participation in Testing

Figure 1:
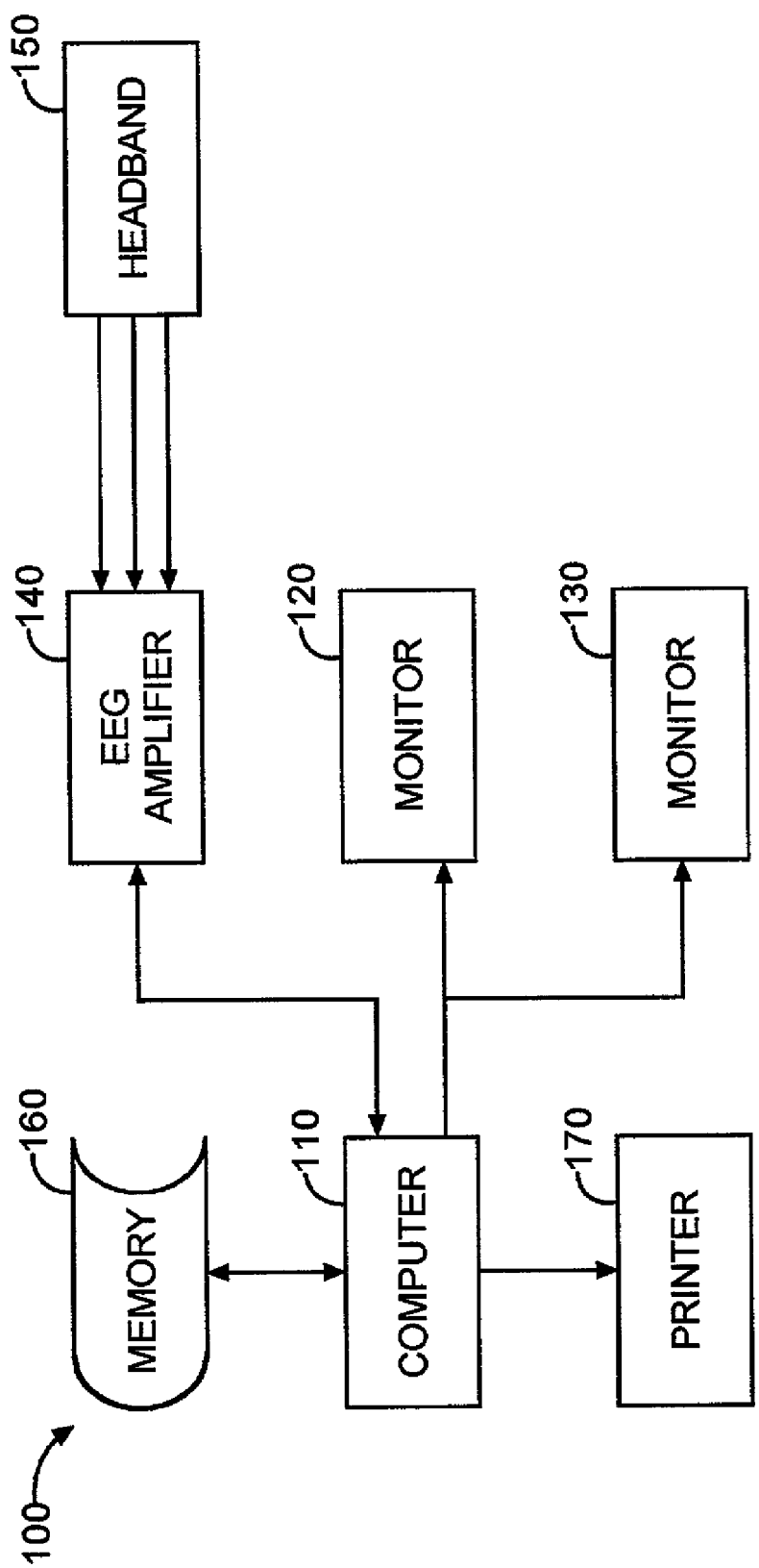
FIG. 1 is a block diagram of an apparatus in accordance with applicant's invention.

Referring to FIG. 1, the Brain Fingerprinting System 100 comprises a personal computer 110 (e.g., Pentium IV, 1 GHz IBM PC); a data acquisition board (e.g., Scientific Solutions Lab Master AD); two monitors 120, 130; a four-channel EEG amplifier system 140 (e.g., Neuroscience); and software for data acquisition and signal processing. The electrodes to used to measure electrical brain activity are held in place by a special headband 150 designed and constructed by the inventor for this purpose. The software presents the stimuli, collects the electroencephalographic data, and analyzes the data.

Stimulus duration of the visual stimuli, e.g., a picture or a word presented on a computer screen, is relatively brief, e.g., 300 msec. It will be understood that stimuli can also be presented through the auditory modality, e.g., as auditory verbal stimuli presented through headphones. Inter-stimulus interval, or stimulus onset asynchrony, is about 2-3 seconds from the onset of one stimulus to the next stimulus onset. The length of the inter-stimulus interval selected depends primarily on the stimulus characteristics: a longer inter-stimulus interval is used when the stimuli are more complex and therefore take longer for the subject to process.

Brain electrical activity is recorded from three midline scalp locations on the head: frontal (Fz), central (Cz) and parietal (Pz), referenced to linked ears or linked mastoids (behind the ear). It will be understood that additional brain signals measured from other scalp locations may be used as well. Electrical activity generated by eye movements is recorded by an electrode above one eye.

Brain electrical activity is amplified, analog filtered (e.g., low-pass 30 Hz, high pass 0.1 Hz) digitized (e.g., at 333 Hz), analyzed on-line, and stored on a memory device 160. Each trial consists of the brain activity recorded in conjunction with one stimulus presentation, about 2 seconds of data.

The full set of stimuli is randomized and the stimuli are presented to the subject one at a time on a video monitor 120. Once all of the stimuli have been S presented, they are randomized again and presented again. This is repeated until a specified number of trials have been presented, or until a sufficient number of artifact-free trials have accumulated.

During data collection, the stimuli are displayed to the subject on one video monitor 120, and the experimenter views another monitor 130. Operator displays include 1) the same thing the subject sees, 2) summary textual information, and 3) waveform displays.

In addition to displaying the results of the analysis on the monitor 130, the system may also print out on a printer 170 the statistical results, the summary of the textual information, and the waveform displays.

Figure 2:
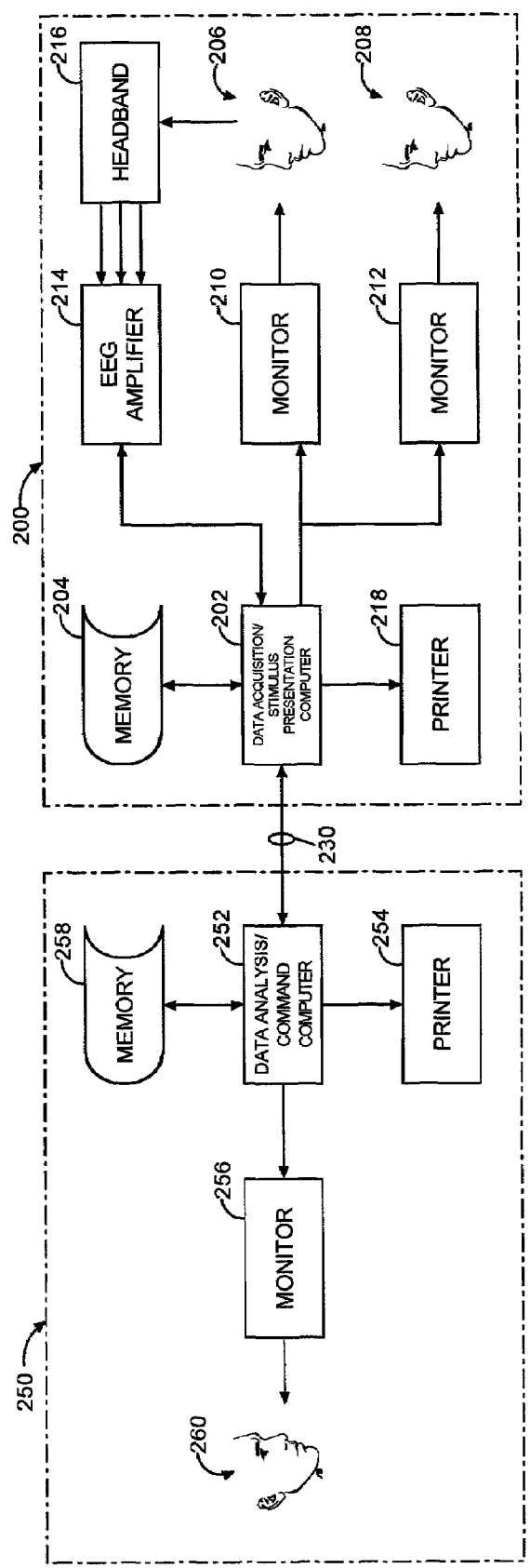
FIG. 2 is a schematic of the operation of an apparatus in accordance with applicant's invention from a remote site.

The previous state of the art in Brain Fingerprinting involved a single system deployed at the location of the subject. There are numerous situations in which it would be optimal to deploy only the necessary part of the system locally, and accomplish the balance of the tasks remotely. Referring to FIG. 2, the stimulus presentation can take place at the local site 200 where the subject 206 is located. The local site 200 contains components that are similar in operation and function to those disclosed in FIG. 1. The local site 200 comprises a local computer 202 for data acquisition and stimulus presentation, which is similar in operation and function to the computer 110 in FIG. 1; two local monitors 210, 212, which are similar in operation and function to the two monitors 120, 130 disclosed in FIG. 1; a four-channel EEG amplifier system 214, which is similar in operation and function to the EEG amplifier system 140 disclosed in FIG. 1; a headband 216, which is similar in operation and function to the headband 150 disclosed in FIG. 1; and a local printer 218, which is similar in operation and function to the printer 170 disclosed in FIG. 1.

Data analysis and/or stimulus set construction can take place remotely at a remote site 250. A remote expert 260 can oversee a local test in real time, viewing data via a remote monitor 256, and can transmit not only guidance to the local personnel 208, regarding the conduct of a test, through a remote data link. Also, remote commands can be transmitted from the remote site 250 from a remote computer (a data analysis/command computer) 252 to a local computer (a data acquisition/stimulus presentation computer) 202 through a remote data link 230, regarding the conduct of the test. In addition to displaying the results of the analysis on the remote monitor 256, the system may also print out on a remote printer 254 the statistical results, the summary of the textual information, and the waveform displays.

This remote interaction allows for efficient use of the time of the most highly trained and qualified system experts. Top experts can remain at a headquarters site, while individuals with lesser expertise can conduct tests at local sites throughout the world with real-time participation and oversight from headquarters. Another advantage of such a division of the system is enhanced safety and convenience for the system experts, when the technology is applied, for example, in prisons, overseas locations, or combat situations. Moreover, situations may arise in which a local expert 208 has specific necessary organizational affiliations, clearances, or other factors affecting access, while the remote expert has a higher level of expertise. A division of the system will allow us to take advantage of both.

Obviously, it is necessary for the stimuli to be presented at the local site 200, where the subject 206 is located. It is necessary to have a direct, local connection with the subject's head to measure the brain waves. It is necessary—or at least extremely desirable with respect to obtaining a clear signal— to amplify and digitize the brain responses locally. Once this has been accomplished, and the data are in the local computer 202, as much information as is necessary for the task at hand—oversight, data analysis, etc.—can be transmitted to the remote site 250. Brain electrical activity that is amplified and analog filtered may be stored by a local memory device 204 or a remote memory device 258. Moreover, commands can be transmitted from the remote site 250 to the local site 200 through a remote data link 230 prior to or during the test itself. Where necessary or useful, a one-way or two-way video and/or audio link can be provided between the local site 200 and the remote site 250. This remote data link 230 can provide for observation and/or communication between a remote expert 260 and the local expert 208 and/or subject 206.

The newest Brain Fingerprinting system is designed to provide for remote access through telephone lines, through radio and satellite communications, and, where available, through high-speed internet links and virtual private networks 3. Data Analysis Algorithms The basic bootstrapping data analysis algorithm previously incorporated in Brain Fingerprinting has proved to be highly effective in classifying subjects in the studies conducted to date. Bootstrapping is described in U.S. Pat. No 5,406,956, col. 73 line 65-col. 74 line 55, and in claim 8 of that patent. Claims 8, 9, and 10 of that patent taken together describe bootstrapping on weighted double-centered correlations. Weighted double-centered correlations are correlations between pairs of waveforms which have the grand mean waveform subtracted from each waveform before computing the correlation.

Additional, more sophisticated data analysis techniques, however, can enhance the effectiveness of the system. These techniques include bootstrapping on unweighted double centered correlations, bootstrapping on single centered correlations, bootstrapping on positive and negative areas and peaks, covariance with a template, stepwise linear discriminant analysis, dynamical systems (chaos) analysis, frequency domain analysis, bootstrapping on the frequency spectra, time-frequency analysis, and combined analysis of multiple electrodes.

Bootstrapping can be implemented using a variety of different metrics for the probe, target, and irrelevant waveforms and the relationships between these waveforms. A modification of the standard algorithm which may improve accuracy is to use bootstrapping on unweighted double-centered waveforms. Unweighted double-centered waveforms are computed as follows. First, average probe, target, and irrelevant waveforms are computed. Then the average of these three waveforms is computed. This average is subtracted from each waveform before computing the correlations This is different from weighted double-centered correlations, because the grand mean subtracted in weighted double-centered waveforms is disproportionately influenced by the trial type (ordinarily, irrelevant), which has the largest number of trials, whereas in unweighted double-centered correlations the mean is equally influenced by targets, probes, and irrelevant, regardless of the number of each type of trials.

Bootstrapping on unweighted double-centered waveforms is the preferred method. This method improves the accuracy of the procedure by giving equal weight to the three trial types, while highlighting the differences in trial types by subtracting the grand mean.

The procedure of bootstrapping on single-centered correlations comprises the same bootstrapping procedure, computed on waveforms from which the mean of all points in each individual waveform (not the grand mean across waveforms) has been subtracted from each point.

Bootstrapping on positive areas is a procedure of bootstrapping applied to the sum of the data points in a time range in which a positive electrical potential is expected, and the waveform is generally positive, i.e., the voltage at the scalp is positive. Similarly, Bootstrapping on negative areas is a procedure of bootstrapping applied to the sum of the data points in a time range in which a negative electrical potential is expected, and the waveform is generally negative, i.e., the voltage at the scalp is negative.

Bootstrapping on a combination of positive and negative areas is a procedure of summing positive and negative areas (after reversing the sign of the negative areas) and computing the bootstrap statistic on this sum.

Bootstrapping on positive peaks is a procedure of computing the bootstrap statistic based on the most positive point in a particular time range. Bootstrapping on negative peaks is a procedure of computing the bootstrap statistic based on the most negative point in a particular time range. Bootstrapping on the difference between positive and negative peaks constitutes computing the bootstrap statistic on the difference between the most positive point in a specific range and the most negative point in a different time range, e.g., the peak of the early positive component of the MERMER and the peak of peak of the late negative component of the MERMER.

In an alternative embodiment, covariance or correlation with a template is be used either with or without bootstrapping to estimate the brain responses to the different stimulus types and the similarity of the waveforms of the different types. A standard template can be derived from a compilation or average of the data of many subjects, from the data of the current subject in response to a known task, or from a mathematical approximation (e.g., part of a sine wave) of the expected brain responses. Covariance or correlation is then computed in the standard manner according to standard statistics.

Bootstrapping is ordinarily computed on waveforms in the time domain. In an alternative embodiment, the waveforms are be transformed from the time domain to the frequency domain, e.g., by a discrete Fourier transform. This allows the analysis to detect phasic differences in frequency-domain activity that are eliminated in the signal-averaging process when time-domain signals are averaged because these frequency-domain phenomena are not phase-locked to the time of the stimulus. When this transformation to the frequency domain is combined with bootstrapping, the contribution of these differences to the distinction between responses to the different trial types can be assessed.

4. Stimulus Presentation Methods, Modalities, and Parameters

The optimum methods, modalities, and parameters for stimulus presentation can be optimized to improve the effectiveness of Brain Fingerprinting. Various modalities of presentation can be applied, and the results analyzed to optimize the system for specific applications. These include visual words, pictorial stimuli, auditory words, and simultaneous auditory and visual presentation. In the auditory modality, the time course and phonological and semantic complexity of the stimuli can be optimized. In the visual pictorial modality, the size, luminance, complexity, content, and composition will be manipulated systematically to titrate the optimum stimulus presentation methods for specific applications. In the visual linguistic modality, the phonological, visual, and semantic complexity; length and time course; size, font, color, luminance, and other physical parameters can be manipulated, and results recorded and analyzed so as to optimize system performance and brain-wave clarity, distinctiveness, and signal-to-noise ratio.

The minimum, maximum, and optimum time course of stimulus events can also be optimized with respect to the number of stimuli required, the number of repetitions of each stimulus, the number and timing of blocks of stimuli, stimulus duration, and interstimulus interval, by systematically manipulating these parameters to titrate optimum performance in a given setting.

B. Medical Applications of Brain Waves

In addition to the forensic application of Brain Fingerprinting, new developments in neuroscience can provide highly valuable applied technologies in several fields of human endeavor. Some these applied technologies are described below.

1. Alzheimer's and Effective Brain Functioning

In the past, diagnosis of Alzheimer's, tracking of the progress of the disease, and evaluation of the effectiveness of treatments were accomplished primarily on the basis of subjective evaluation based on observation of behavior and secondhand reports from caretakers or family members regarding their subjective evaluations of observations of behavior. Currently available methods have very limited specificity, objectivity, and accuracy, and cannot be applied quickly.

Measurements of brain activity promise to provide an alternative or supplement to available techniques that has the desirable features of objectivity and specificity, and can be applied quickly.

The application of brain waves in Alzheimer's and other disease processes has the following basic phases.

a. Establish the specific deficits in brain functioning that characterize the disease—e.g., specific cognitive processing and memory deficits. (This has been largely accomplished in the case of Alzheimer's.)

b. Assign specific information-processing tasks that are known to apply the faculties in which these deficits occur.

c. Measure brain activity during these tasks that provides an objective index of the effectiveness of the brain processes involved.

It is well known that the normal process of aging involves a generalized slowing of mental and physical processes. Alzheimer's and other specific disease processes, by contrast, produce a slowing of certain cognitive functions, but not of peripheral motor processes. Brain-wave measurements can provide a means of determining objectively and quantitatively which processes are slowing in a specific individual, and how much. This provides an objective measure regarding the diagnosis of disease processes such as Alzheimer's, the evaluation of the progress of the disease process, and the effectiveness of drugs and other treatments in delaying or reversing the progress of the disease.

For example, research has established that the latency of the P300 component of the event-related potential (a major brain response used in Brain Fingerprinting) provides an index of the speed of cognitive stimulus evaluation, separate from response selection and execution. A subject may be assigned a cognitive task that involves evaluating a stimulus (say, a phrase or picture flashed on a computer screen), selecting a response (say, a button press with one or the other thumb, depending on certain characteristics of the stimulus), and executing the response (pressing a button with the thumb). The normal aging process will slow all phases of accomplishing this task, including the muscle activities involved in moving the thumb. The cognitive deficits produced by Alzheimer's will not slow the motion of the thumb, but will slow the cognitive process of stimulus evaluation, particularly when the task involves memory. Brain-wave measurements provide an objective index of this specific phase of cognitive processing, which is unavailable through behavioral measures alone.

In the preferred embodiment, this is accomplished in the following way. A subject is presented with a set of items to remember, referred to herein as a memory set. In the preferred embodiment, the memory set consists of a series of words or phrases such as the names of various geographical locations or common items. Pictures may also be used. Then a series of stimuli (e.g., words or phrases) is presented briefly (e.g., for 0.3 seconds) one at a time (e.g., one item every 2 seconds) on a computer screen. Some of the items in the sequence are in the memory set, and some are not. The subject is instructed to press a button (e.g., with the left thumb) when an item from the memory set appears on the screen, and another button (e.g., with the right thumb) when an item not in the memory set appears. Reaction times and event-related brain potentials are recorded.

The task the subject must undertake involves the following phases:

A. Stimulus evaluation processes
 1. Stimulus encoding: the stimulus is perceived and recognized
 2. Memory search: Is it in the memory set?
B. Response selection and execution processes
 3. Response selection: decide on left or right button press
 4. Response execution: push the button Reaction time provides a measure of the time taken to accomplish all of these tasks in series, that is, the sum of the times for the individual tasks. In normal aging, overall reaction time slows down. Brain-wave measurements allow us to determine which phases in the process contribute to this slowing, and how much different phases contribute. This is important, because cognitive deficits such as those brought about by Alzheimer's differentially affect different phases of the process, and will affect phases of the process that are unaffected by normal aging.

Previous research on event-related potentials, reaction time, and aging points to the following conclusions regarding the slowing that takes place with normal aging:

1. Stimulus evaluation is slowed.
 2. The memory search is NOT slowed by normal aging. To the extent that memory-related cognitive processes have deteriorated due to disease processes such as Alzheimer's, the memory search IS slowed.
 3. Response selection is slowed in normal elderly people, but not only because of cognitive slowing. There is also considerable evidence that older people adopt a more conservative strategy, that is, they respond more slowly to make sure that they are giving the correct response. There is always a trade-off between speed of response and accuracy, and older people tend to favor accuracy at the expense of speed.
 4. Response execution, that is, pushing the button, is slowed in the elderly due to slower motor processes, including the neuronal and muscular processes involved.

Brain-wave responses can add to our understanding and measurement of this process, and to the contribution of cognitive deficits due to diseases such as Alzheimer's, due to the following factors: 1) brain-wave measurements can provide an index not only of the whole process, but of individual phases of the overall process; and 2) certain phases of this process—specifically, the memory search—are affected by cognitive deficits such as those brought about by Alzheimer's but not by normal aging. To accomplish the goal of revealing cognitive deficits such as those caused by Alzheimer's, and distinguishing such cognitive deficits from the generalized slowing that takes place in aging, we must independently manipulate and measure the different phases of this process.

The primary process of interest for the evaluation of cognitive deficits such as those resulting from Alzheimer's is the memory search, phase 2 of the above process. In this phase a subject must conduct a search of his memory to determine whether or not the item presented is in the memory set. As noted above, brainwave research has shown that this memory search is not slower with normal aging. If there has been cognitive deterioration due to diseases such as Alzheimer's that affect memory, however, this memory search will be slowed. In this case, phase 2 will be slowed, the slowing of this phase will contribute to an overall slowing of reaction time. Overall reaction time, however, is also slowed by normal age-related changes in phases 1, 3, and 4 that do not involve any pathology.

If we measure only overall reaction time, we have no way of knowing whether the slow responses (and the additional incremental slowing of responses with increase in the memory set size) result from ineffective memory search in phase 2 brought about by cognitive deficits, or from slowness in some other phase that may be brought about by normal aging in the absence of any pathology. How do we measure the slowing that results specifically from pathological cognitive deficits that will interfere with the memory search phase of the task, and not from the slowness associated with normal aging that will retard the other phases of the task?

This is where brain responses provide a unique and otherwise unavailable solution. Research has shown that the latency of the P300 (or P3) component of the event-related potential is affected by stimulus evaluation, and not by response selection and execution. This means that the P300 latency will be affected by how long it takes the subject to recognize the stimulus, and by the time taken for the memory search to decide whether the presented item is in the memory set. P300 latency will not be affected by how long it takes the person to select his response and push the button.

Overall reaction time will be slowed in an elderly individual whether there is pathological cognitive deterioration or not. To the extent that there has been cognitive deterioration, memory search will be slowed, and P300 latency will be slowed. To isolate the effect of pathological cognitive deterioration—which, unlike normal aging, will retard the memory search—it is necessary to manipulate this specific phase of the task, while leaving the other phases of the task the same, and to measure the effect this manipulation has on the brain responses.

This is accomplished by varying the size of the memory set. If the memory set contains only one item, then the subject must search only one item to determine if it is in the memory set or not. If the set size is increased, one item at a time, up to six items, the memory search task requirement will increase in increments. The P300 latency will increase in increments, each increment representing the time it takes for the subject to search memory for one item.

In this way the latency of the P300 component of the brain response, and specifically the incremental variation in latency with incremental increases in the size of the memory set, provides a measure of the cognitive deficits affecting memory, a measure that is independent of and unaffected by other factors unrelated to memory. These other factors include the general slowing (e.g., of the thumb and of the initial stimulus recognition), the more conservative response strategy, and the incremental slowing in response selection with increased task difficulty. All of these other factors take place in normal aging, and do not indicate any pathological cognitive deficit.

Cognitive deficits such as those produced by Alzheimer's will affect the time it takes to accomplish the memory search involved in this task, and specifically the increase in time it takes for the memory search as each new item is added to the memory set. This effect can be effectively measured by measuring P300 latency. The latency of the P300 component provides an index of stimulus evaluation time. The incremental increases in P300 latency with incremental increases in memory set size provide an index of the time consumed by the memory search. This brainwave-based metric provides insight into the locus of cognitive slowing, and the degree to which it is a result disease processes such as Alzheimer's rather than normal aging.

Reaction time alone does not provide a means to differentiate between pathological slowing of the memory-search processes that takes place with cognitive deficits (but not with normal aging) on the one hand, and slowing of other phases that takes place with normal aging whether there are pathological cognitive deficits or not on the other hand. In normal aging, reaction time in this task is slowed due to several factors: a) slowness in phase 1, stimulus encoding, b) slowness in phase 3, response selection, c) slowness in phase 4, response execution. Brain-wave research has shown that the memory search is not slowed in normal aging. In normal aging, however, the response selection phase is slowed incrementally more when the task is made incrementally more difficult, e.g., when the memory set size is increased. This incremental slowing in phase 3 is confounded with the memory-search slowing in phase 2 when reaction time alone is measured. This makes it impossible to measure the timing of the memory search—which is affected by cognitive deficits but not by normal aging—through measuring reaction time alone.

Brain-wave measurements provide a direct means to measure the specific slowing associated with the memory search, and thus to isolate the contribution of memory-related cognitive deficits such as those resulting from Alzheimer's to overall slowing in task performance. Thus, brain-wave measurements, combined with a sophisticated series of task manipulations, provide a uniquely effective method of assessing cognitive deficits such as those resulting from Alzheimer's.

Presenting a memory-search task and varying the size of the memory set is one method of manipulating the cognitive difficulty of the task. There are numerous other ways to accomplish this. In an alternative embodiment, the subject is assigned a task involving distinguishing cognitive categories, such as verbs versus nouns, and responding differentially to stimuli based on their categories. This manipulation will affect the difficulty of stimulus evaluation, and therefore will affect P300 latency. The task difficulty is varied by varying the categorization rule, for example, by requiring categorization of transitive versus intransitive verbs, a more difficult distinction than nouns versus verbs, or by varying the items or type of items to be recognized and categorized. In another alternative embodiment, the subject is assigned a memory-related task involving recognition of items that are commonly remembered (e.g., the subject's address, the names of relatives, specific major life events), and the cognitive difficulty of the task is varied by varying factors affecting the memorability of items to be recognized (e.g., by presenting items that are less salient for the subject). In each case, brain wave measurements can provide a metric of the speed and effectiveness of implementation of the cognitive task, and of the impact on cognitive functioning of increasing the task difficulty. Thus, cognitive deficits resulting from disease processes or injury can be detected and quantified.

Other brain-wave techniques can provide objective measurements of other cognitive processes that are affected by the disease. Research has shown that dynamical systems analysis (chaos mathematics) can provide a measure of the orderliness and complexity of the brain processes involved in a specific subject's implementation of a specific cognitive task—independent of any behavioral measures involved. Multifaceted electroencephalographic response analysis (MERA), a patented process of brain-wave measurement invented by the inventor of Brain Fingerprinting, provides yet another means of measuring the orderliness of cognitive processes that is objective and independent of behavioral measures. Both of these techniques can be applied to investigate the specific deficits associated with Alzheimer's, and to provide indices for use in diagnosis, evaluation of the progress of the disease, and evaluation of the effectiveness of treatment.

Application of brain waves in the diagnosis of Alzheimer's and other cognitive disorders involves a comprehensive investigation of cognitive deficits associated with Alzheimer's and other disease processes, isolating the brain responses that most accurately index these cognitive deficits, developing protocols for diagnosis, tracking of the degenerative progress of the disease, and using brainwave measurements to provide an objective measure of cognitive functioning and hence of the effectiveness of treatments. This technology includes the following:

A. Event-related potential indices of specific cognitive processes involved in the degenerative processes associated with Alzheimer's.
B. Event-related potential indices of memory deficits associated with Alzheimer's.
C. Event-related potential protocols for diagnosis and evaluation of the progress of the disease.
D. Objective evaluation of the effectiveness of drugs and other interventions using event-related potentials.
E. Dynamical systems analysis techniques for assessing cognitive functioning and the effect of disease processes, and cognitive deficits in orderliness and complexity of thinking in Alzheimer's.
F. Dynamical systems analysis protocols for diagnosis and evaluation of the progress of the disease.
G. Objective evaluation of the effectiveness of drugs and other interventions using dynamical systems analysis.
H. Multifaceted electroencephalographic response analysis (MERA) techniques for assessing cognitive functioning and the effect of disease processes.
I. MERA protocols for diagnosis and evaluation of the progress of the disease.
J. Objective evaluation of the effectiveness of drugs and other interventions using MERA.

C. Brain Fingerprinting as a Forensic Technology

The central problem in investigating crimes is twofold: 1) to identify the perpetrators of past criminal acts and those who provided support and planning for them, and 2) to identify trained criminals who are planning future criminal acts. Brain Fingerprinting addresses both of these needs.

1. Investigation of Criminal Act

The fundamental difference between a perpetrator of a criminal act and an innocent person who may be a suspect is that the perpetrator, having committed the crime, has a record of that event stored in his brain, and the innocent suspect does not. Until the invention of Brain Fingerprinting, there was no scientific way to detect this fundamental difference. By detecting the presence or absence of information stored in the brain, Brain Fingerprinting provides an accurate, scientific solution to a central problem in the fight against crime.

Scientific research and actual applications have proven that Brain Fingerprinting detects information stored in the human brain with high accuracy by measuring electrical brain responses to information presented on a computer screen. The brain response to known information—that is, information that matches the information stored in the brain—is clearly distinguishable from the brain response to unknown or irrelevant information.

In tests on FBI agents, in real-life situations, and in actual criminal cases, Brain Fingerprinting has proven to be extremely accurate and effective in detecting information stored in the brain regarding actual crimes and many other situations. In the same way, this scientific technology can be used to identify those who have perpetrated specific criminal acts or have helped in the planning of these acts. Brain Fingerprinting thus can provide a key capability in the investigation of crimes.

Once a criminal act has occurred, the investigators are often able to discover extensive evidence of not only the act itself, but the support and planning that led up to the crime. Once these details are known, Brain Fingerprinting can be used to detect not only direct perpetrators of the crime act who may have survived (if any), but also anyone who has participated in the planning, training, and support activities necessary to perpetrate the large-scale crime.

As investigators unveil criminal activity more and more information will become known that can identify the people involved. Brain Fingerprinting can determine objectively who has and does not have knowledge of the inner workings of specific criminal act—incriminating information that is known to those who play a role in the criminal activities (and those who investigate them), and not to innocent people who may appear suspicious for innocent reasons such as race, ethnicity, dress or way of life, or unknowing contact with criminals.

In organized and large-scale crimes, often the masterminds who conceive and plan the crimes send others to actually commit the crimes. In this way the masterminds can avoid detection and continue to create criminal activities even if the hands-on perpetrators are caught or do not survive. These criminal masterminds, conspirators, and planners may not have direct participation in the end criminal act—which would make them vulnerable to detection by external physical evidence or eyewitnesses—but they nevertheless do have a record of the details of the crime or series of crimes that would be known only to those intimately involved. By detecting this information in the brain, Brain Fingerprinting provides an effective means to detect not only the hands-on perpetrators, but those who actually conceive, create, and plan crimes.

2. Detecting Criminals Before they Strike

Brain Fingerprinting can not only detect the perpetrators and planners of past crimes, it can also detect those trained to perpetrate crimes before they strike. The fundamental difference between a member of an organized crime organization and an innocent person is that the criminal has critical information regarding criminal organizations and plans that an innocent person does not have. If Brain Fingerprinting can detect an FBI agent by measuring brain responses to information known only to FBI agents, it can use the same technology to detect a criminal who has had specific criminal training or indoctrination not known to the general public, or is familiar with the inner workings of an organized criminal organization. This can be accomplished by measuring brain responses to information uniquely known to such individuals. Brain Fingerprinting can detect the presence or absence of this information, and thus distinguish the criminal from the innocent person. Criminals can be dealt with appropriately. Innocent people who may have fallen under suspicion for any reason can be cleared of suspicion and allowed to go on with their lives.

Like any other science, it is necessary to apply Brain Fingerprinting carefully and intelligently. Prior to administering a Brain Fingerprinting test, investigators must ascertain if there is any non-crime-related reason why an individual has had access to information of interest in that specific investigation. Obviously, if someone is an expert in criminology and has studied organized crime, he will have information about organized crime that the general public does not know. He may know details about specific crimes because of participation in the investigation of these crimes. In such a case, Brain Fingerprinting would not be applicable. If, on the other hand, a suspected organized crime boss claimed to know nothing about an organized crime conspiracy involving a series of crimes, Brain Fingerprinting could be used to determine if in fact he had such "guilty knowledge."

3. Brain Fingerprinting is not Applicable for General Screening.

The term "screening" is most commonly used to refer to a general screening program, where the investigators do not know specifically what they are seeking to detect. General screening must be distinguished from specific screening, which is described below. An example of general screening is pre-employment or periodic screening for a position requiring a high security clearance, in which authorities may seek to determine whether the applicant has financial problems, drug or alcohol problems, past criminal activities of any sort, deviant behavior, intention to cause harm to the organization in any way, or any one of a myriad of other activities that may tend to compromise the position of the applicant or make him or her susceptible to pressure to violate the trust he or she is to be given. Brain Fingerprinting is not applicable in such a general screening program. When authorities do not know what specific activities or information they are looking for, there is no way of determining what to test for. Clearly, it is not feasible to construct a set of stimuli for every imaginable experience an applicant or employee might have had that would be of concern to the investigating organization.

4. Brain Fingerprinting is Highly Effective and Accurate for Specific Screening.

In specific screening applications the investigators are looking for specific knowledge, information, or expertise that is possessed by certain individuals—e.g., members of a specific organized crime organization—and not by others. In many situations, particularly in the investigating criminal activity, investigators have a good idea of what they are looking for. In situations where the investigators have a reasonable idea of what they are looking for, Brain Fingerprinting can be of tremendous value. This was proven in the FBI agent study in which Brain Fingerprinting distinguished between FBI agents and non-agents.

Like any other scientific technology, Brain Fingerprinting must be intelligently and carefully. There will, of course, be cases where someone who is not a criminal has considerable specific knowledge about organized criminal activities and training. For example, a university professor or a military or law enforcement expert may have studied the subject in some detail This does not present a problem. People who have a legitimate reason for having specific crime-related knowledge can be identified by interviews, and, when necessary and appropriate, by checking their background and the accuracy of their stories.

5. Preserving Human Rights

While identifying criminal perpetrators, it is also vitally important to preserve human rights and to minimize the trauma for innocent suspects. Brain Fingerprinting addresses both of these needs. Brain Fingerprinting is noninvasive, non-stressful, and non-testimonial An innocent person simply views a series of words, phrases, or pictures on a computer screen, and does not even know which ones are relevant to a crime or a criminal. His lack of recognition of the crime-relevant information will be revealed in his brain responses, and thus an innocent person can be exonerated with a minimum of stress and trauma, while his or her human rights and human dignity are preserved.

In the case of an actual criminal being tested with Brain Fingerprinting, if it is applied early enough to detect a person involved in a plan to commit a crime before he strikes, Brain Fingerprinting can be used to avoid damage to life and property—of such a crime. If it is used to detect the perpetrators and planners of criminal acts that have already occurred, Brain Fingerprinting will serve to free society from any further damage from these criminals by helping to bring the criminals to justice.

D. Applications of Brain Waves in Advertising, Training, and Education

In the forensic applications described above, brain-wave measurements are used to determine what information is stored in a particular brain. In the medical applications described above, brain-wave measurements are used to diagnose disease processes based on measuring the brain-wave manifestations of the cognitive and memory deficits caused by the disease process. Similarly, brain measurements are used to track the progress of disease and evaluate the effectiveness of treatment.

In evaluation of training and educational programs and also in the evaluation of the effectiveness of advertising, the critical variable to measure is not what the subject knows, or how effectively the subject is functioning, but rather how effective a particular advertisement or training protocol is in imparting information and stimulating attention, understanding, and retention of material. In other words, forensic applications evaluate what a person knows; medical applications evaluate how effectively a person cognitively processes, learns, and remembers things. The task in evaluating educational, training, and advertising programs is to determine how effective a particular program is in stimulating a person to attend to, process, and retain information.

The same brain-wave responses as those used in medical applications, and similar protocols, are used in the preferred embodiment in the evaluation of advertising and training materials. In medical applications, the technique is to use a standard input, and evaluate how each person responds. In the evaluation of training, education, and advertising, the technique is to vary the input provided to a group of normal subjects, and evaluate the impact of the different information-presentation options by measuring the different brain responses they produce. These brain responses provide an objective measure of whether and to what degree the input is producing the desired impact on the viewer.

In evaluating, for example, a training or educational video or a television advertisement, first we want to know if the medium is effective in stimulating the viewer to pay attention. Second, we want to know if the viewer notices and cognitively processes the critical features presented—e.g., the brand-name product or the critical training information. Third, we want to know if this critical information is retained.

Event-related brain potentials, dynamical systems analysis, and multifaceted electroencephalographic response analysis (MERA) all are known to be capable of providing an objective measure of the level of attention a subject is paying to a particular set of stimuli. Al of these technologies have also been shown to be effective in evaluating the level, complexity, and orderliness of cognitive processing. Event-related potentials and MERA have been shown to provide effective measures of what specific items a person notices and processes. Event-related potentials and MERA have also been shown to be effective in evaluating memory processes.

In the preferred embodiment, these brain-wave measurements are applied during the viewing of the advertising, educational, or training media to evaluate the attention and processing elicited by these materials, and to evaluate what specifically in the presentation the subjects are attending to, processing, and taking note of. Brain-wave measurements are also applied in testing after the exposure to the advertising, training, or educational media to evaluate what the subjects have retained from that exposure. Using standard protocols, tests can be applied efficiently in a widespread manner.

Application of brain waves in the evaluation of advertising, training, and educational materials involves the following:

A. Assessment of the effectiveness of ads in eliciting attention by measuring event-related brain potentials.

B. Assessment of the effectiveness of ads in eliciting attention through MERA.

C. Assessment of the effectiveness of ads in eliciting attention through dynamical systems analysis.

D. Assessment of the effectiveness of educational and training materials in eliciting attention by measuring event-related brain potentials.

E. Assessment of the effectiveness of educational and training materials in eliciting attention through MERA.

F. Assessment of the effectiveness of educational and training materials in eliciting attention through dynamical systems analysis.

G. Assessment of the effectiveness of ads in eliciting relevant cognitive processing by measuring event-related brain potentials.

H. Assessment of the effectiveness of ads in eliciting relevant cognitive processing through MERA.

I. Assessment of the effectiveness of ads in eliciting relevant cognitive processing through dynamical systems analysis.

J. Assessment of the effectiveness of educational and training materials in eliciting relevant cognitive processing by measuring event-related brain potentials.

K. Assessment of the effectiveness of educational and training materials in eliciting relevant cognitive processing through MERA.

L. Assessment of the effectiveness of educational and training materials in eliciting relevant cognitive processing through dynamical systems analysis.

M. Assessment of the effectiveness of ads in creating salience and memorability of critical items by measuring event-related brain potentials.

N. Assessment of the effectiveness of ads in creating salience and memorability of critical items through MERA.

O. Assessment of the effectiveness of ads in creating salience and memorability of critical items through dynamical systems analysis.

P. Assessment of the effectiveness of educational and training materials in creating salience and memorability of critical items by measuring event-related brain potentials.

Q. Assessment of the effectiveness of educational and training materials in creating salience and memorability of critical items through MERA.

R. Assessment of the effectiveness of educational and training materials in creating salience and memorability of critical items through dynamical systems analysis.

Summary of Major Advantages of the Invention

After reading and understanding the foregoing description of preferred embodiments of the invention, in conjunction with the illustrative drawings, it will be appreciated that several distinct advantages of the subject a method and apparatus for Brain Fingerprinting, measurement, assessment and analysis of brain function is obtained.

One advantage of the present invention is that it provides a means for diagnosing cognitive disorders and making assessments of treatment effectiveness for such disorders.

Another advantage of the present invention is that it provides a means of determining objectively and quantitatively which mental and physical processes are slowing in a specific individual, and how much.

Yet another advantage of the present invention is that it provides a means for developing evidence for use in forensic science.

A further advantage of the present invention is that it allows for evaluation of advertising, education, and training.

In accordance with the foregoing, the present invention provides a method and apparatus for Brain Fingerprinting, measurement, assessment and analysis of brain function in aging and Alzheimer's disease.

In describing the invention, reference has been made to preferred embodiments and illustrative advantages of the invention. Those skilled in the art, however, and familiar with the instant disclosure of the subject invention, may recognize additions, deletions, modifications, substitutions and other changes that fall within the purview of the subject invention.

OTHER PUBLICATIONS

The disclosures of the following publications are incorporated by reference into the specification.

Farwell, L. A., Chambers, R. D., Miller, G. A., Coles, M. G. H., and Donchin, E. (1985).
A Specific Memory Deficit in Elderly Subjects Who Lack A P300.
*Psychophysiology*, 23, 589 (Abstract.)
Donchin, E., Miller, G. A., and Farwell, L. A. (1986a)
The Endogenous Components of the Event-Related Potential—A Diagnostic Tool?
In *Advances in Brain Research*, 1986. Amsterdam: Elsevier.
Donchin, E., Miller, G. A., and Farwell, L. A. (1986b)
The Endogenous Components of the Event-Related Potential—A Diagnostic Tool?
In *Progress in Brain Research, Vol. 70: Aging of the Brain and Alzheimer's Disease*, D. F. Swaab, E. Fliers, M. Mirmiran, W. A. Van Gool, and F. Van Haaren, eds. Amsterdam: Elsevier.
Farwell, L. A. and Donchin, E. (1986)
The "Brain Detector:" P300 in the Detection of Deception.
*Psychophysiology*, 23, 4: 434 (Abstract).
Farwell, L. A., Donchin, E., and Kramer, A. F. (1986)
Talking Heads: A Mental Prosthesis for Communicating with Event-Related Brain Potentials of the EEG.
*Psychophysiology*, 23, 4: 434 (Abstract).
Bashore, T. R., Miller, G. A., Farwell, L. A., and Donchin, E. (1987).
Research in Geriatric Psychophysiology.
In *Annual Review of Gerontology and Geriatrics*. New York: Springer.
Farwell, L. A. and Donchin, E. (1988)
Talking Off The Top Of Your Head: A Mental Prosthesis Utilizing Event-Related Brain Potentials.
*Electroencephalography and Clinical Neurophysiology*, 70: 510-513.
Farwell, L. A. and Donchin, E. (1988)
Event-Related Brain Potentials in Interrogative Polygraphy: Analysis Using Bootstrapping.
*Psychophysiology*, 25, 4: 445 (Abstract).
Farwell, L. A. and Donchin, E. (1989)
Detection of Guilty Knowledge with ERPs.
*Psychophysiology*, 26, 4A: S8 (Abstract of an address presented at the Twenty-Eighth Annual Meeting of the Society for Psychophysiological Research, October, 1989.)
Farwell, L. A. and Donchin, E. (1991)
The Truth Will Out: Interrogative Polygraphy ("Lie Detection") With Event-Related Brain Potentials.
*Psychophysiology*, 28:531-547.
Farwell, L. A. (1992)
The Brain-wave Information Detection (BID) System: A New Paradigm for Psychophysiological Detection of Information.
Doctoral Dissertation, University of Illinois at Urbana-Champaign, 1992.
Farwell, L. A. (1992)
The Farwell System for Event-Related Brain Potential Information Detection: A New Paradigm in Psychophysiological Detection of Concealed Information.
Technical Report prepared for the Office of Research and Development of the Central Intelligence Agency, 1992.
Farwell, L. A. (1992)
Two New Twists on the Truth Detector: Brain-wave Detection of Occupational Information.
*Psychophysiology*, 29,4A: S3 (Abstract of an address presented at the Thirty-Second Annual Meeting at the Society for Psychophysiological Research, October 1992.)
Farwell, L. A., Martinerie, J. M., Bashore, T. R., and Rapp, P. E. (1993)
Optimal Digital Filters for Long Latency Event-Related Brain Potentials.
*Psychophysiology*, 30, 3, 306-315.
Rapp, P. E., Albano, A. M., Schmah, T. I., and Farwell, L. A. (1993)
Filtered Noise Can Mimic Low Dimensional Chaotic Attractors.
*Physical Review E*, 47,4, 2289-2297.
Farwell, L. A. and Richardson, D. A. (1993)
Detection of FBI Agents with the Farwell MERA System: A New Paradigm for Psychophysiological Detection of Concealed Information.
Technical Report, Human Brain Research Laboratory, Inc.
Farwell, L. A. (1993)
Brain MERMERs: Detection of FBI Agents and Crime-Relevant Information with the Farwell MERA System.
*Proceedings of the International Security Systems Symposium*, Washington, D.C.
Farwell, L. A. and Hernandez, R. (1993)
Brain-Wave Detection of Concealed Information.
Technical Report #92*F138600*000 prepared for the Office of Research and Development of the Central Intelligence Agency.
Farwell, L. A. and Farwell, G. W. (1995)
Quantum-Mechanical Processes and Consciousness.
*Bulletin of the American Physical Society*, 40, 2, 956-57.
Farwell, L. A. and Smith, S. S. (2001).
Using Brain MERMER Testing to Detect Concealed Knowledge Despite Efforts to Conceal.
*Journal of Forensic Sciences* 46,1: 135-143

What is claimed:

1. A method of using electrical brain responses to quantitatively evaluate effectiveness and speed of cognitive brain functioning for the purpose of measuring at least one of the following:
    level of cognitive functioning, cognitive deficits; efficacy of treatments for cognitive deficits; mental deterioration due to disease processes; mental deterioration due to trauma; mental deterioration due to aging; mental deterioration due to Alzheimer's disease; and efficacy of treatments for said mental deterioration; comprising:
    assigning a cognitive task that has cognitive and non-cognitive aspects, wherein said cognitive task includes recognizing and responding to autobiographically relevant items or events experienced during at least one life experience of a subject as a means at least to invoke the subject's episodic memory; and a difficulty of said cognitive aspect depends on at least one factor affecting memorability of the items; and wherein said cognitive aspect also involves classifying and differentially responding to the items according to a classification rule, and a difficulty of said cognitive task depends on at least one of the classification rule, the items to be classified, a number of the items to be classified, and a type of the items to be classified;
    measuring behavioral output of said cognitive task and a timing of said output;
    measuring and analyzing brain responses that provide an index of the effectiveness or speed of specific cognitive processes; and
    quantitatively evaluating the effectiveness and speed of cognitive brain functioning and deficits based on said brain responses and said analyzing.

2. A method according to claim 1 wherein the cognitive difficulty of said cognitive task is systematically manipulated by presenting subjects with at least two tasks with at least two different cognitive difficulties, and the effect of such manipulation on said brain responses is measured.

3. A method according to claim 2 wherein the time course of said brain responses is measured, and said evaluating is accomplished using metrics that include differences in said time course.

4. A method according to claim 3 wherein said brain responses are event-related brain potentials.

5. A method according to claim 4 wherein said brain responses include a P300 component.

6. A method according to claim 3 wherein said bran responses include a memory and encoding related multifaceted electroencephalographic response, also known as a MERMER.

7. A method according to claim 2 wherein the analyzing of said brain responses includes frequency-domain and time-domain analysis.

8. A method according to claim 7 wherein the analyzing of said brain responses includes a combination of frequency-domain and time-domain analysis.

9. A method according to claim 2 wherein the analyzing of said brain responses includes dynamical systems analysis, also known as chaos analysis.

10. A method according to claim 2 wherein said cognitive task includes recognizing and responding to items in a memory set, and the difficulty of said cognitive task is manipulated by varying the number of items in said memory set.

11. A method according to claim 2 wherein the difficulty of said cognitive task is manipulated by varying factors affecting memorability of items.

12. A method according to claim 2 wherein the difficulty of said cognitive task is manipulated by at least one of varying the classification rule, varying the items to be classified, varying the number of the items to be classified, and varying the type of the items to be classified.

13. A method according to claim 2, wherein a latency of a P300 component provides the index.

14. A method according to claim 13, wherein the specific cognitive processes are selected from the group consisting of speed of evaluation, speed of memory searching and combinations thereof.

15. A method according to claim 1 wherein the timing of said brain responses is measured, and said evaluation is accomplished using metrics that include differences in the time course of said responses.

16. A method according to claim 15 wherein said brain responses are event-related brain potentials.

17. A method according to claim 16 wherein said bran responses include a P300 component.

18. A method according to claim 15 wherein said brain responses include a memory and encoding related multifaceted electroencephalographic response, also known as a MERMER.

19. A method according to claim 1 wherein the analyzing of said brain responses includes frequency-domain analysis.

20. A method according to claim 19 wherein the analyzing of said brain responses includes a combination of frequency-domain and time-domain analysis.

21. A method according to claim 1 wherein the analyzing of said brain responses includes dynamical systems analysis, also known as chaos analysis.

22. A method according to claim 1, comprising:
    assigning a task that has cognitive and non-cognitive aspects;
    systematically manipulating a cognitive difficulty of the task by presenting subjects with at least two tasks with at least two different cognitive difficulties;
    measuring brain responses to the task;
    generating an index of specific cognitive processes associated with the task; and
    evaluating the speed and effectiveness of cognitive functioning based on the brain responses.

23. A method as recited in claim 22, wherein the evaluation of cognitive functioning includes comparing a time course of brain responses to at least one task with a relatively lower cognitive difficulty with a time course of brain responses to at least one task of a relatively higher cognitive difficulty.

24. A method according to claim 1 for assessing mental deterioration of a subject due to Alzheimer's disease comprising:
    assigning a task that has cognitive and non-cognitive aspects wherein the cognitive task includes recognizing and responding to items relevant to at least one life experience of the subject;
    measuring brain responses to the task;
    generating an index of specific cognitive processes associated with the task; and
    evaluating cognitive functioning based on the brain responses.

25. A method as recited in claim 24, further comprising the step of systematically manipulating a cognitive difficulty of the task by presenting subjects with at least two tasks with at least two different cognitive difficulties.

26. A method as recited in claim 25, wherein a difficulty of the cognitive task is manipulated by varying factors affecting memorability of items.

27. A method as recited in claim 25, wherein the measuring of the brain responses includes a speed and magnitude of the brain responses to determine the speed and effectiveness with which the subject is processing information.

28. A method as recited in claim 24, wherein the evaluation of cognitive functioning is assessment of mental deterioration and includes comparing a time course of brain responses to at least one task with a relatively lower cognitive difficulty with a time course of brain responses to at least one task of a relatively higher cognitive difficulty.

* * * * *